(12) United States Patent
Blalock et al.

(10) Patent No.: US 9,244,160 B2
(45) Date of Patent: Jan. 26, 2016

(54) ULTRASONIC TRANSDUCER DRIVE

(75) Inventors: Travis N. Blalock, Charlottesville, VA (US); William F. Walker, Earlysville, VA (US); John A. Hossack, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1687 days.

(21) Appl. No.: 11/160,914

(22) Filed: Jul. 14, 2005

(65) Prior Publication Data

US 2007/0016044 A1 Jan. 18, 2007

Related U.S. Application Data

(63) Continuation of application No. PCT/US2004/000888, filed on Jan. 14, 2004.

(60) Provisional application No. 60/439,990, filed on Jan. 14, 2003, provisional application No. 60/440,020, filed on Jan. 14, 2003, provisional application No. 60/440,262, filed on Jan. 15, 2003.

(51) Int. Cl.
*A61B 8/00* (2006.01)
*G01S 7/52* (2006.01)

(52) U.S. Cl.
CPC ............ *G01S 7/52017* (2013.01); *A61B 8/4427* (2013.01); *A61B 8/4483* (2013.01); *G01S 7/5208* (2013.01)

(58) Field of Classification Search
CPC ................ A61B 8/4483; A61B 8/4427; G01S 7/52017; G01S 7/5208
USPC ................. 600/437, 440–443, 447, 459–471; 73/626; 327/108, 382

See application file for complete search history.

(56) References Cited

U.S. PATENT DOCUMENTS

| 4,105,018 A | 8/1978 | Greenleaf et al. |
| 4,109,644 A | 8/1978 | Kojima |

(Continued)

FOREIGN PATENT DOCUMENTS

| DE | 19524505 A1 | 11/1996 |
| EP | 0173681 A1 | 5/1996 |

(Continued)

OTHER PUBLICATIONS

Walker, W.F., et al., "The Application of K-Space in Medical Ultrasound", IEEE Ultrasonics Symposium, pp. 1379-1383, (1995).

(Continued)

*Primary Examiner* — Long V Le
*Assistant Examiner* — Colin T Sakamoto
(74) *Attorney, Agent, or Firm* — Schwegman Lundberg & Woessner, P.A.

(57) ABSTRACT

In some illustrative embodiments, an ultrasonic transducer drive includes a signal generator for producing an outgoing signal and a transducer for converting the outgoing signal to outgoing ultrasound. The transducer may also convert at least a portion of ultrasound reflected by an object to an incoming signal. The transducer may have a transmit side connected conductably to the signal generator during at least a first predetermined period of time and a receive side connected conductably to a signal receiver during at least a second predetermined period of time. A shunt may be connectable between the receive side and a reference potential. The signal generator may generate the outgoing signal during at least substantially the first predetermined period of time while the shunt connects the receive side to the reference potential. The signal receiver may receive the incoming signal during substantially the second predetermined period of time while the shunt is substantially open.

35 Claims, 4 Drawing Sheets

(56) References Cited

U.S. PATENT DOCUMENTS

| | | | |
|---|---|---|---|
| 4,275,461 A | 6/1981 | Sternick et al. | |
| 4,338,948 A | 7/1982 | Perez-Mendez et al. | |
| 4,573,477 A | 3/1986 | Namekawa et al. | |
| 4,640,291 A * | 2/1987 | 't Hoen | 600/459 |
| 4,671,293 A * | 6/1987 | Shaulov | 600/447 |
| 4,694,434 A | 9/1987 | von Ramm et al. | |
| 4,817,614 A | 4/1989 | Hassler et al. | |
| 4,867,167 A | 9/1989 | Magnin | |
| 4,870,867 A * | 10/1989 | Shaulov | 73/625 |
| 4,949,310 A | 8/1990 | Smith et al. | |
| 5,014,712 A | 5/1991 | O'donnell et al. | |
| 5,027,821 A | 7/1991 | Hirama et al. | |
| 5,095,890 A | 3/1992 | Houghton et al. | |
| 5,105,814 A | 4/1992 | Drukarev et al. | |
| 5,119,342 A | 6/1992 | Harrison, Jr. et al. | |
| 5,186,177 A * | 2/1993 | O'Donnell et al. | 600/463 |
| 5,230,340 A | 7/1993 | Rhyne | |
| 5,268,876 A | 12/1993 | Rachlin | |
| 5,331,964 A * | 7/1994 | Trahey et al. | 600/447 |
| 5,454,809 A * | 10/1995 | Janssen | 606/41 |
| 5,469,851 A | 11/1995 | Lipschutz | |
| 5,471,990 A | 12/1995 | Thirsk | |
| 5,487,387 A | 1/1996 | Trahey | |
| 5,531,117 A | 7/1996 | Fortes | |
| 5,546,807 A | 8/1996 | Oxaal et al. | |
| 5,566,675 A | 10/1996 | Li et al. | |
| 5,590,658 A * | 1/1997 | Chiang et al. | 600/447 |
| 5,626,576 A * | 5/1997 | Janssen | 606/41 |
| 5,632,277 A | 5/1997 | Chapman et al. | |
| 5,673,699 A | 10/1997 | Trahey et al. | |
| 5,684,484 A | 11/1997 | Suzuki | |
| 5,722,412 A * | 3/1998 | Pflugrath et al. | 600/459 |
| 5,793,701 A | 8/1998 | Wright et al. | |
| 5,797,845 A | 8/1998 | Barabash et al. | |
| 5,801,657 A | 9/1998 | Fowler et al. | |
| 5,817,024 A * | 10/1998 | Ogle et al. | 600/447 |
| 5,882,307 A | 3/1999 | Wright et al. | |
| 5,893,363 A * | 4/1999 | Little et al. | 600/447 |
| 5,924,993 A * | 7/1999 | Hadjicostis et al. | 600/462 |
| 5,947,905 A * | 9/1999 | Hadjicostis et al. | 600/463 |
| 5,997,477 A | 12/1999 | Sehgal | |
| 5,997,479 A | 12/1999 | Savord et al. | |
| 6,013,032 A | 1/2000 | Savord | |
| 6,016,285 A | 1/2000 | Wright et al. | |
| 6,027,447 A | 2/2000 | Li | |
| 6,048,316 A | 4/2000 | Zhao et al. | |
| 6,059,730 A | 5/2000 | Miwa et al. | |
| 6,063,033 A | 5/2000 | Haider et al. | |
| 6,068,597 A | 5/2000 | Lin | |
| 6,071,240 A | 6/2000 | Hall et al. | |
| 6,074,346 A * | 6/2000 | Oppelt | 600/437 |
| 6,120,450 A | 9/2000 | Li | |
| 6,126,602 A | 10/2000 | Savord et al. | |
| 6,135,961 A | 10/2000 | Pflugrath et al. | |
| 6,142,946 A * | 11/2000 | Hwang et al. | 600/459 |
| 6,179,780 B1 | 1/2001 | Hossack et al. | |
| 6,203,498 B1* | 3/2001 | Bunce et al. | 600/446 |
| 6,251,074 B1 | 6/2001 | Averkiou et al. | |
| 6,276,211 B1 | 8/2001 | Smith | |
| 6,380,766 B2* | 4/2002 | Savord | 327/108 |
| 6,383,139 B1* | 5/2002 | Hwang et al. | 600/441 |
| 6,416,475 B1* | 7/2002 | Hwang et al. | 600/441 |
| 6,423,002 B1* | 7/2002 | Hossack | 600/439 |
| 6,443,896 B1 | 9/2002 | Detmer | |
| 6,443,900 B2* | 9/2002 | Adachi et al. | 600/458 |
| 6,450,960 B1 | 9/2002 | Rather et al. | |
| 6,471,651 B1* | 10/2002 | Hwang et al. | 600/459 |
| 6,482,160 B1 | 11/2002 | Stergiopoulos et al. | |
| 6,491,634 B1 | 12/2002 | Leavitt et al. | |
| 6,537,219 B2 | 3/2003 | Poland et al. | |
| 6,540,677 B1* | 4/2003 | Angelsen et al. | 600/437 |
| 6,572,547 B2 | 6/2003 | Miller et al. | |
| 6,582,372 B2 | 6/2003 | Poland | |
| 6,641,534 B2 | 11/2003 | Smith et al. | |
| 6,650,264 B1 | 11/2003 | Chan et al. | |
| 6,669,641 B2 | 12/2003 | Poland et al. | |
| 6,692,439 B1 | 2/2004 | Walker et al. | |
| 7,064,700 B1 | 6/2006 | Garrity et al. | |
| 7,402,136 B2 | 7/2008 | Hossack et al. | |
| 2002/0144549 A1 | 10/2002 | Yao | |
| 2004/0000841 A1* | 1/2004 | Phelps et al. | 310/314 |
| 2005/0154300 A1* | 7/2005 | Wodnicki et al. | 600/437 |
| 2007/0016022 A1 | 1/2007 | Blalock et al. | |
| 2012/0053460 A1 | 3/2012 | Blalock et al. | |

FOREIGN PATENT DOCUMENTS

| | | |
|---|---|---|
| EP | 0713681 B1 | 7/2007 |
| WO | WO-2004064619 A2 | 8/2004 |
| WO | WO-2004064619 A3 | 8/2004 |
| WO | WO-2004064620 A2 | 8/2004 |
| WO | WO-2004064620 A3 | 8/2004 |
| WO | WO-2004065978 A2 | 8/2004 |
| WO | WO-2004065978 A3 | 8/2004 |

OTHER PUBLICATIONS

Robinson, Marshal T., et al., "Real-Time Angular Scatter Imaging System for Improved Tissue Contrast in Diagnostic Ultrasound Images", IEEE Transactions on Ultrasonics and Frequency Control, vol. 41, No. 1, Jan. (1994).

Jensen, J., et al., "Calculation of Pressure Fields from Arbitrarily Shaped, Apodized, and Excited Ultrasound Transducers", IEEE Transactions on Ultrasonics, Ferroelectrics, and Frequency Control, vol. 39, No. 2, Mar. (1992).

Linzer, M., et al., "Phase Aberration Corrections and Algorithm Using Near-Field Signal Redundancy Method: Algorithm", Ultrasonic Imaging, vol. 17, 45-65, (1995).

Walker, W.F., et al., "Speckle Coherence and implications for adaptive imaging", J. Acoust. Soc. Am., vol. 101, No. 4, Apr., (1994).

Ng, Gary, et al., "A Speckle Target Adaptive Imaging Technique in the Presence of Distributed Aberrations", IEEE Transactions on Ultrasonics, Ferroelectrics, and Frequency Control, vol. 44, No. 1, Jan., (1997).

Campbell, J.A., et al., "Measurements of Calf liver ultrasonic differential and total scattering cross sections", J. Acoust. Soc. Am., vol. 45, No. 2, Feb., (1994).

Nassiri, D.K. et al., "The Use of Angular Acoustic Scattering Measurements to Estimate Structural parameters of Human and Animal Tissues", J. Acoust. Soc. Am., vol. 79, No. 6, Jun., (1986).

Davros, W.J., et al., "Frequency-dependent angular scattering of Ultrasound by Tissue-Mimicking materials and Excised tissue", J. Acoust. Soc. Am., vol. 80, No. 1, Jul., (1986).

Rachlin, Daniel, "Direct Estimation of Aberrating Delays in Pulse-echo Imaging Systems", J. Acoust. Soc. Am., vol. 88, No. 1, Jul. (1990).

Lacefield, J.C., "Angular Scatter Ultrasound Imaging using Separated Arrays", Thesis, Duke University, (1999).

"U.S. Appl. No. 10/542,242, Non Final Office Action mailed Dec. 1, 2006", 8 pgs.

"U.S. Appl. No. 10/542,242, Notice of Allowance mailed Jun. 15, 2007", 5 pgs.

"U.S. Appl. No. 10/542,242, Preliminary Amendment filed Jul. 14, 2005", 3 pgs.

"U.S. Appl. No. 10/542,242, Response filed Apr. 2, 2007 to Non Final Office Action mailed Dec. 1, 2006", 10 pgs.

"U.S. Appl. No. 11/160,915, Non Final Office Action mailed Feb. 17, 2011", 11 pgs.

"U.S. Appl. No. 11/160,915, Non Final Office Action mailed Jun. 28, 2010", 8 pgs.

"U.S. Appl. No. 11/160,915, Response filed Feb. 12, 2010 to Restriction Requirement mailed Jan. 12, 2010", 15 pgs.

"U.S. Appl. No. 11/160,915, Response filed Oct. 28, 2010 to Non Final Office Action mailed Jun. 28, 2010", 11 pgs.

"U.S. Appl. No. 11/160,915, Restriction Requirement mailed Jan. 12, 2010", 6 pgs.

"U.S. Appl. No. 13/210,890, Examiner Interview Summary mailed Jul. 2, 2013", 4 pgs.

(56) References Cited

OTHER PUBLICATIONS

"U.S. Appl. No. 13/210,890, Final Office Action mailed Oct. 25, 2013", 7 pgs.
"U.S. Appl. No. 13/210,890, Final Office Action mailed Dec. 31, 2013", 15 pgs.
"U.S. Appl. No. 13/210,890, Non Final Office Action mailed May 8, 2013", 12 pgs.
"U.S. Appl. No. 13/210,890, Non Final Office Action mailed Aug. 14, 2014", 16 pgs.
"U.S. Appl. No. 13/210,890, Preliminary Amendment filed Aug. 16, 2011", 10 pgs.
"U.S. Appl. No. 13/210,890, Response filed Jun. 30, 2014 to Final Office Action mailed Dec. 31, 2013", 13 pgs.
"U.S. Appl. No. 13/210,890, Response filed Aug. 8, 2013 to Non Final Office Action mailed May 8, 2013", 14 pgs.
"Canadian Application Serial No. 2,513,447, Office Action mailed Apr. 9, 2014", 3 pgs.
"Canadian Application Serial No. 2,513,447, Response filed Oct. 9, 2014 to Office Action mailed Apr. 9, 2014", 24 pgs.
"European Application Serial No. 04702168.8, European Search Report mailed May 27, 2009", 4 pgs.
"European Application Serial No. 04702168.8, Office Action mailed Aug. 10, 2011", 4 pgs.
"European Application Serial No. 04702168.8, Office Action mailed Sep. 3, 2009", 6 pgs.
"European Application Serial 04702168.8, Response filed Apr. 13, 2010 to Office Action mailed Sep. 3, 2009", 91 pgs.
"European Application Serial No. 04702168.8, Response filed Sep. 12, 2011 to Office Action mailed Aug. 10, 2011", 13 pgs.
"European Application Serial No. 04702545.7, European Search Report mailed Jun. 5, 2007", 3 pgs.
"European Application Serial No. 04702545.7, Office Action mailed Jul. 13, 2010", 8 pgs.
"European Application Serial No. 04702545.7, Office Action mailed Sep. 26, 2007", 4 pgs.
"European Application Serial No. 04702545.7, Response filed Apr. 4, 2008 to Office Action mailed Sep. 26, 2007", 28 pgs.
"International Application Serial No. PCT/US2004/000887, International Preliminary Report on Patentability mailed Jul. 15, 2005", 4 pgs.
"International Application Serial No. PCT/US2004/000887, Written Opinion mailed Nov. 1, 2004", 3 pgs.
"International Application Serial No. PCT/US2004/000888, International Preliminary Report on Patentability mailed Jul. 15, 2005", 4 pgs.
"International Application Serial No. PCT/US2004/000888, Written Opinion mailed Sep. 7, 2004", 3 pgs.
"International Application Serial No. PCT/US2004/001002, International Preliminary Report on Patentability mailed Nov. 21, 2008", 6 pgs.
"International Application Serial No. PCT/US2004/001002, Written Opinion mailed Aug. 20, 2004", 5 pgs.
"Philips' New 3D Technology Puts the Beating Heart in Physicians' Hands", Philips Medical Systems Press Release. Business Wire, (Nov. 15, 2002), 4 pgs.
Anderson, et al., "A Handle-Mounted Multiplexing Pre-amplifier for Synthetic Receive Aperture Imagining", 19th Annual Symposium on Ultrasonic Imagine and Tissue Characterization vol. 16, (1994), 55.
Blalock, T. N., et al., "A 1.5 GOPS Analog CMOS Array Processor with Integrated Optical Image Acquisition for Position Encoding Applications", Proc. of the Int. Sym. on VLSI Circuits, (1998), 204-205.
Blalock, T. N, et al., "True Color 1024x768 Microdisplay with Analog In-Pixel Pulse Width Modulation and Retinal Averaging Offset Correction", IEEE Journal of Solid-State Circuits 36(5), (May 2001), 838-845.
Davidsen, et al., "Sparse Geometrics for two dimensional array transducers in volumetric imaging", IEEE Ultrasonics symposium, (1993), 1091-1094.

Emery, Charles, et al., "Ultrasonic imaging using a 5-MHz multilayer/single-layer hybrid array for increased signal-to-noise ratio", IEEE Transactions on Ultrasonics, Ferroelectrics, and Frequency Control 46(5), (1999), 1101-1119.
Fabian, C. M, et al., "Development of a Parellel Acquisition System for Ultrasound Research", Proc. SPIE. vol. 4325. Medical Imaging: Ultrasonic Imaging and Signal Processing, (2001), 54-62.
Foster, et al., "A digital annular array prototype scanner for realtime ultrasound imaging", Ultrasound in Medicine and Biology 15(7), (1989), 661-672.
Fritsch, et al., "Beamforming with a reduced sampling rate", Ultrasonics, IPC Science and Technology Press ltd. 40(1-8), (2002), 599-604.
Fuller, et al., "A Portable, Low-Cost, Highly Integrated, 3D Medical Ultrasound System", IEEE Ultrasonics Symposium vol. 1, (2003), 38-41.
Kasai, Chihiro, et al., "Real-Time Two-Dimensional Blood Flow Imaging Using an Autocorrelation Technique", IEEE, vol. SU-32, No. 3, (May 1985), pp. 458-464.
Kim, Joo Han, et al., "Pipelined sampled-delay focusing in ultrasound imaging systems", Ultrasonic Imaging Dynamedia inc 9(2), (1987), 75-91.
Kleinfelder, et al., "A 10k Frames per Second 0.18 Micron CMOS Digital Pixel Sensor with Pixel-Level Memory", Proc. of ISSCC Solid-State Circuits Conference, (2001), 88-89 and 435-436.
Kwon, O, et al., "A Novel Double Slope Analog-toDigital Converter for a High Quality 640x480 CMOS Imaging System", Proc. of the 6th Int. Conf on VLSI and CAD, (1999), 335-338.
Lee, W, et al., "Real Time Three Dimensional Intracardiac Echocardiography for Guidance of Cardiac Interventional Procedures", Presented at IEEE Ultrasonics Symposium, (2001), 1307-1310.
Light, E, et al., "Real-time three-dimensional intracardiac echocardiography", Ultrasound in Medicine and Biology 27(9), (2001), 1173-1183.
Light, E, et al., "Two dimensional arrays for real time volumetric and intracardiac imaging with simultaneous electrocardiogram", Presented at IEEE Ultrasonics Symposium, (2000), 1195-1198.
Light, E, "Update of two dimensional arrays for real time volumetric and real time intracardiac imaging", Presented at IEEE Ultrasonics Symposium, (1999), 1217-1220.
Lockwood, et al., "Optimizing the radiation Pattern of Sparse Periodic Linear Arrays", IEEE Transactions on Ultrasonics, Ferroelectrics and Frequency Control 43(1), (1996), 7-14.
Magnin, et al., "Frequency compounding for speckle contrast reduction in phased array images", Ultrasonic Imaging 4, (1982), 267-281.
Mann, J. A, et al., "A Constrained Adaptive Beamformer for Medical Ultrasound", 2002 IEEE Ultrasonics Symposium, 2002. Proceedings, vol. 2, (2002), 1807-1810.
Melton, et al., "A-mode speckle reduction with compound frequencies and compund band-widths", Ultrasonic Imagining 6, (1984), 159-173.
Mills, D, et al., "Multi-Layered PZT/polymer composites to increase signal-to-noise ratio and resolution for medical ultrasound transducers. II. Thick film technology", IEEE Transactions on Ultrasonics, Ferroelectrics, and Frequency Control 49(7), (2002), 1005-1014.
O'Donnell, et al., "Optimum displacement for compound image generation in medical ultrasound", IEEE Transactions on Ultrasonics, Ferroelectrics, and Frequency Control 35(4), (1988), 470-476.
Plummer, et al., "Two-dimensional Transmit/Receive Ceramic Piezoelectric Arrays: Construction and Performance", IEEE Transactions on Sonics and Ultrasonics vol. SU-25(5), (1978), 273-280.
Ranganathan, et al., "A Novel Beamformer Design Method for Medical Ultrasound. Part II: Simulation Results", IEEE Transactions on Ultrasonics, Ferroelectrics, and Frequency Control 50(1), (2003), 25-39.
Ranganathan, et al., "A Novel Beamformer Design Method for Medical Ultrasound: Part I: Theory", IEEE Transactions on Ultrasonics, Ferroelectrics, and Frequency Control 50(1), (Jan. 2003), 15-24.
Ranganathan, K., et al., "Direct sampled I/Q beamforming for compact and very low-cost ultrasound imaging", IEEE Trans Ultrason Ferroelectr Freq Control., 51(9), (Sep. 2004), 1082-94.

(56) References Cited

OTHER PUBLICATIONS

Trahey, et al., "A quantitative approach to speckle reduction via frequency compounding", Ultrason. Imag. 8, (1986), 151-164.

Trahey, et al., "Speckle pattern correlation with lateral aperture translation: experimental results and implications for spatial compounding", IEEE Transactions on Ultrasonics, Ferroelectrics, and Frequency Control vol. UFFC-33(3), (May 1986), 257-264.

Von Ramm, et al., "Real time volumetric ultrasound imagining system", Journal of Digital Imaging 3(4), (1990), 261-266.

Von Ramm, Olaf T, et al., "High-speed ultrasound volumetric imaging system. II. Parallel processing and image display", IEEE Transactions on Ultrasounics, Ferroelectrics, and Frequency Control 38(2), (Mar. 1991), 109-115.

Walker, William, "A New Class of APerture Domain Flow Estimation Algoithms", Proc. IEEE Ultrason. Symp. 2, (1997), 1227-1231.

Yang, D.X.D, et al., "A Nyquist-Rate Pixel-Level ADC for CMOS Image Sensors", IEEE Journal of Solid-State Circuits 34(3), (Mar. 1999), 348-356.

Ziomek, et al., "Digital I/Q Demodulator", Proceedings of the 1995 Particle Accelerator Conference. vol. 4., 2663-2665.

"U.S. Appl. No. 13/210,890, Examiner Interview Summary mailed Mar. 25, 2015", 2 pgs.

"U.S. Appl. No. 13/210,890, Final Office Action mailed Mar. 25, 2015", 20 pgs.

"U.S. Appl. No. 13/210,890, Response filed Feb. 17, 2015 to Non Final Office Action mailed Aug. 14, 2014", 14 pgs.

"Canadian Application Serial No. 2,513,447, Office Action mailed Apr. 2, 2015", 4 pgs.

"Multiply Your Sampling Rate with Time-Interleaved Data Converters", Maxim Integrated, Tutorial 989, (Mar. 1, 2001), 6 pgs.

\* cited by examiner

ULTRASONIC TRANSDUCER DRIVE

CROSS-REFERENCE TO RELATED APPLICATIONS

The present application is a continuation of International Application No. PCT/US2004/000888 filed Jan. 14, 2004, which claims priority to U.S. Provisional Application Ser. Nos. 60/440,020 filed on Jan. 14, 2003, 60/439,990 filed on Jan. 14, 2003, and 60/440,262 filed on Jan. 15, 2003 the entire disclosures of which are incorporated herein by reference.

BACKGROUND

1. Field of the Invention

The present invention relates to ultrasonic diagnostic imaging systems and methods. More specifically, the preferred embodiments relate to a device and method for driving an ultrasound transducer that may be incorporated in a substantially integrated hand held ultrasonic diagnostic imaging instrument.

2. Introduction

Medical imaging is a field dominated by high cost systems that may be so complex as to require specialized technicians for operation and the services of experienced medical doctors and nurses for image interpretation. Medical ultrasound, which is considered a low cost modality, utilizes imaging systems costing as much as $250K. These systems may be operated by technicians with two years of training or specialized physicians. This high-tech, high-cost approach works very well for critical diagnostic procedures. However it makes ultrasound impractical for many of the routine tasks for which it would be clinically useful.

A number of companies have attempted to develop low cost, easy to use systems for more routine use. The most notable effort is that by Sonosite. Their system produces very high quality images at a system cost of approximately $20,000. While far less expensive than high-end systems, these systems are still very sophisticated and require a well-trained operator. Furthermore, at this price few new applications may be opened.

Many ultrasonic imaging systems utilize an array transducer that is connected to beamformer circuitry through a cable, and a display that is usually connected directly to or integrated with the beamformer. This approach is attractive because it allows the beamformer electronics to be as large as is needed to produce an economical system. In addition, the display may be of a very high quality. Conventional system configurations can be awkward to use because of the lengthy cable involved. Finally, the typical large size of the beamformer limits the system's portability.

A schematic diagram of a transducer drive 100 for a conventional phased array ultrasound system is shown in FIG. 1. A piezoelectric transducer array 102, shown on the left, acts as an interface to a signal processor by converting electrical signals to acoustic pulses and vice versa. Images may be formed by transmitting a series of acoustic pulses from the transducer array 102 and displaying signals representative of the magnitude of the echoes received from these pulses. A beamformer 114 applies delays to the electrical signals to steer and focus the acoustic pulses and echoes.

Image formation begins when a state of a transmit/receive switch (TX/RX switch) 104 is altered to connect the transducer elements 102 to individual transmit circuits. Next, transmit generators 106 output time varying waveforms with delay and amplitude variations selected to produce a desired acoustic beam. Voltages of up to 100 Volts may be applied to the transducer elements 102. Once transmission is complete, the state of the TX/RX switch 104 is altered again to connect the transducer elements 102 to individual receive circuitry associated with each element.

Signals representative of incoming echoes may be amplified by pre-amplifiers 108 and automatic gain control (AGC) 110 circuits to compensate for signal losses due to diffraction and attenuation. Note that the transducer array 102 shown in FIG. 1 has one common electrode 112, and the non-common electrodes may be multiplexed between high-voltage transmit and low-voltage receive signals. This conventional TX/RX switch 104 is the source of considerable expense and bulk in typical ultrasound systems.

Ultrasonic transducers associated with ultrasound imaging systems may be driven from a single terminal with the second terminal grounded. A transducer may be used to transmit ultrasound signals as well as receive reflected ultrasound.

A signal received at a transducer may typically be several orders of magnitude smaller than the signal that was transmitted due to, inter alia, signal attenuation by the target tissue. Some of the signal may be lost due to transducer inefficiencies as well. It may be thus necessary to couple the transducer to a high-voltage transmit signal while the ultrasound is being transmitted, and then to a sensitive low-noise preamplifier while the reflected ultrasound is being received.

A switch that couples the transducer to the transmit and receive signals must be capable of withstanding high peak transmit voltages (typically 50-200 volts) while isolating the preamplifier input from those voltage levels, since they would otherwise destroy the preamplifier. If a receiver for the signals from the transducers is fabricated as a high-density, low-voltage integrated circuit (IC), the switches themselves may need to be fabricated off-chip in a separate package from materials and devices that can withstand the high voltage transmit pulses.

Some conventional system architectures have been improved upon through reductions in beamformer size. One of the most notable efforts has been undertaken by Advanced Technologies Laboratories and then continued by a spin-off company, Sonosite. U.S. Pat. No. 6,135,961 to Pflugrath et al., entitled "Ultrasonic Signal Processor for a Hand Held Ultrasonic Diagnostic Instrument" hereby incorporated by reference herein in its entirety, describes some of the signal processing employed to produce a highly portable ultrasonic imaging system. The Pflugrath '961 patent makes reference to an earlier patent, U.S. Pat. No. 5,817,024 to Ogle et al., entitled "Hand Held Ultrasonic Diagnostic instrument with Digital Beamformer" hereby incorporated by reference herein in its entirety. In U.S. Pat. No. 6,203,498 to Bunce et al., entitled "Ultrasonic Imaging Device with Integral Display" hereby incorporated by reference herein in its entirety, however, the transducer, beamformer, and display may be all integrated to produce a very small and convenient imaging system.

Other references of peripheral interest are U.S. Pat. No. 6,669,641 to Poland, et al., entitled "Method of and system for ultrasound imaging" which describes an ultrasonic apparatus and method in which a volumetric region of the body is imaged by biplane images. One biplane image has a fixed planar orientation to the transducer, and the plane of the other biplane image can be varied in relation to the fixed reference image.

U.S. Pat. No. 6,491,634 to Leavitt, et al., entitled "Sub-beam-forming apparatus and method for a portable ultrasound imaging" describes a sub-beam-forming method and apparatus that is applied to a portable, one-dimensional ultrasonic imaging system. The sub-beam-forming circuitry may be included in the probe assembly housing the ultrasonic transducer, thus minimizing the number of signals that are communicated between the probe assembly and the portable processor included in the imaging system.

U.S. Pat. No. 6,380,766 to Savord, entitled "Integrated circuitry for use with transducer elements in an imaging system" describes integrated circuitry for use with an ultrasound transducer of an ultrasound imaging system.

U.S. Pat. No. 6,013,032 to Savord, entitled "Beam-forming methods and apparatus for three-dimensional ultrasound imaging using two-dimensional transducer array" describes an ultrasound imaging system including a two-dimensional array of ultrasound transducer elements that define multiple sub-arrays, a transmitter for transmitting ultrasound energy into a region of interest with transmit elements of the array, a sub-array processor and a phase shift network associated with each of the sub-arrays, a primary beam-former and an image generating circuit.

U.S. Pat. No. 6,126,602 to Savord, et al., entitled "Phased array acoustic systems with intra-group processors" describes an ultrasound imaging apparatus and method that uses a transducer array with a very large number of transducer elements or a transducer array with many more transducer elements than beam-former channels.

U.S. Pat. No. 5,997,479 to Savord, et al., entitled "Phased array acoustic systems with intra-group processors," describes an ultrasound imaging apparatus and method that uses a transducer array with a very large number of transducer elements or a transducer array with many more transducer elements than beamformer channels.

U.S. Pat. No. 6,582,372 to Poland, entitled "Ultrasound system for the production of 3-D images" describes an ultrasound system that utilizes a probe in conjunction with little or no specialized 3-D software/hardware to produce images having depth cues.

U.S. Pat. No. 6,179,780 to Hossack, et al., entitled "Method and apparatus for medical diagnostic ultrasound real-time 3-D transmitting and imaging," describes a medical diagnostic ultrasound real-time 3-D transmitting and imaging system that generates multiple transmit beam sets using a 2-D transducer array.

U.S. Pat. No. 6,641,534 to Smith, et al., entitled "Methods and devices for ultrasound scanning by moving sub-apertures of cylindrical ultrasound transducer arrays in two dimensions" describes methods of scanning using a two dimensional (2-D) ultrasound transducer array.

U.S. Pat. No. 4,949,310 to Smith, et al., entitled "Maltese cross processor: a high speed compound acoustic imaging system" describes an electronic signal processing device which forms a compound image for any pulse-echo ultrasound imaging system using a two-dimensional array transducer.

U.S. Pat. No. 6,276,211 to Smith, entitled "Methods and systems for selective processing of transmit ultrasound beams to display views of selected slices of a volume" describes the selection of a configuration of slices of a volume, such as B slices, I slices, and/or C slices.

U.S. Pat. No. 6,074,346 to Oppelt, entitled "Transmit/receive ultrasound front end circuit providing automatic transmit/receive switching" describes a transmit/receive circuit employing passive elements.

Commercial ultrasound systems have been limited to one-dimensional (1-D) or linear transducer arrays until fairly recently. A typical number of transducers in such an array may be 128. Providing separate multiplex and receive circuitry is manageable with this many transducers, albeit with significant use of expensive high-voltage switches. Newer arrays, however, may be likely to be two-dimensional (2-D) or square arrays. The number of transducers in a two-dimensional array may range up to 128×128 or 16,384, and is often in the thousands. Maintaining separate current receive, transmit, and multiplex partitioning for the transducers in such an array creates a tremendous burden in terms of cost, space, and complexity. The mass and volume of thousands of high-voltage multiplexes is enough to discourage the use of two-dimensional arrays in portable ultrasound imaging systems.

Accordingly, existing ultrasound systems with thousands of separate transmit and receive switches may be too expensive for many applications. While a variety of systems and methods may be known, there remains a need for improved systems and methods.

BRIEF DESCRIPTION OF THE DRAWINGS

The preferred embodiments of the present invention are shown by a way of example, and not limitation, in the accompanying figures, in which.

SUMMARY OF THE INVENTION

Figure 1:
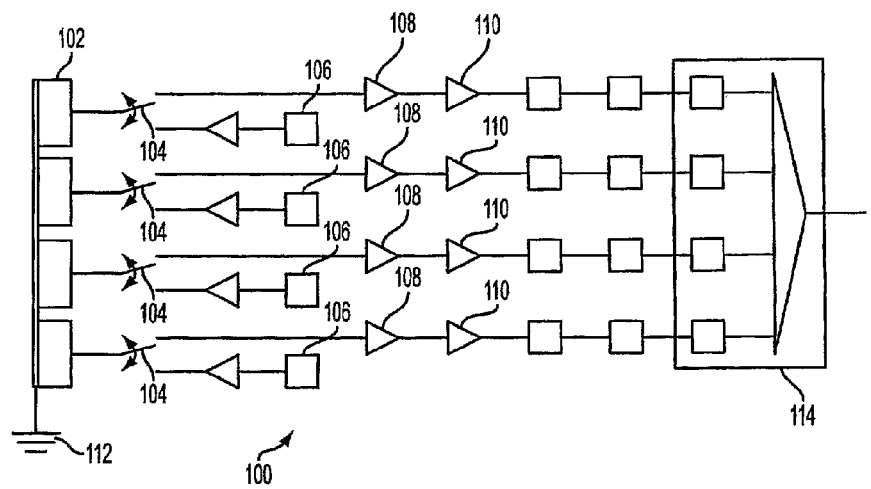
FIG. 1 is a schematic diagram of a conventional ultrasonic transducer drive.

The present invention ultrasonic transducer drive may be incorporated in an ultrasonic imaging system convenient enough to be a common component of nearly every medical examination and procedure. The present invention ultrasonic transducer drive provides the potential to have a broad and significant impact in healthcare. The instant document identifies various clinical applications of the present invention ultrasonic transducer drive, but should not be limited thereto, and other applications will become attained as clinicians gain access to the system and method.

The preferred embodiments of the present invention may improve significantly upon existing methods and/or apparatuses. In particular, the present invention comprises an ultrasonic transducer drive that may be used in a hand held ultrasonic instrument such as one provided in a portable unit which performs B-mode or C-Mode imaging and collects three dimensional (3-D) image data.

According to some embodiments, an ultrasonic transducer drive is provided that includes, in a first aspect of the invention, a signal generator for producing an outgoing signal, a transducer for converting the outgoing signal to outgoing ultrasound and for converting at least a portion of reflected ultrasound to an incoming signal, the transducer having a transmit side and a receive side, the transmit side connected conductably to the signal generator during at least a first predetermined period of time, the receive side connected conductably to a signal receiver during at least a second predetermined period of time, and a shunt connectable between the receive side and a reference potential, wherein the signal generator generates the outgoing signal during at least substantially the first predetermined period of time while the shunt connects the receive side to the reference potential, and wherein the signal receiver receives the incoming signal during substantially the second predetermined period of time while the shunt is substantially open.

In a second aspect of the invention, a method of driving an ultrasonic transducer includes generating an outgoing signal, connecting a receive side of a transducer to a reference potential, transducing the outgoing signal to outgoing ultrasound with the transducer, disconnecting the receive side of the transducer from the reference potential, receiving at least a portion of reflected ultrasound at the transducer, transducing the reflected ultrasound to an incoming signal with the transducer, and converting the incoming signal to an image.

In a third aspect of the invention, a system for driving an ultrasonic transducer includes means for generating an outgoing signal, means for transducing the outgoing signal to outgoing ultrasound and reflected ultrasound to an incoming signal, means for connecting a receive side of the transducer means to a reference potential, means for disconnecting the receive side of the transducer means from the reference potential, and means for converting the incoming signal to an image.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

DETAILED DESCRIPTION OF THE PREFERRED EMBODIMENTS

The device and method for driving an ultrasound transducer may be utilized with various products and services as discussed below, but is not limited thereto. The device and method for driving an ultrasound transducer may enable substantially fully integrated interfacing between high density 2-D transducer arrays and receive circuits fabricated as integrated circuits (IC) without individual high voltage switches on each channel. In one embodiment, the transducer element is a floating device. In this embodiment, a high voltage transmit signal may be coupled to one side of each transducer while low-voltage signals may be received from the other side of the transducer, instead of providing a single common node for an array of transducers. In this embodiment the receive circuitry may only have to deal with current pulses rather than high voltage pulses, thus substantially simplifying the design of the receiver protection circuits.

Technicians may attempt to insert needles into a vein based on the surface visibility of the vein coupled with their knowledge of anatomy. While this approach works quite well in thin, healthy individuals, it can prove extremely difficult in patients who may be ill or obese. It may be desirable to have a relatively small, inexpensive, and portable ultrasound imaging system for guiding the insertion of intravenous (IV) devices like needles and catheters into veins, or for drawing blood.

Sleep apnea (obstruction of the air passage in the of the throat) may affect more than eighteen million Americans. Obstructive sleep apnea may be among the most common variants of sleep apnea. Obstructive sleep apnea may represent a significant risk to the patient. It is difficult and expensive to diagnose obstructive sleep apnea. Typical diagnostic methods require an overnight hospital stay in an instrumented laboratory. Many at-risk patients refuse this inconvenient testing regime and thus go undiagnosed. It may be desirable to have a relatively small, inexpensive, and portable ultrasound imaging system to aid in the diagnosis of obstructive sleep apnea in a minimally obtrusive manner.

Manual palpation is an exceedingly common diagnostic procedure. Clinicians use their sense of touch to feel for subcutaneous lumps or even to estimate the size of lymph nodes or other masses. While palpation undoubtedly yields valuable qualitative information, numerous studies have shown it to have extremely poor sensitivity and that quantitative size estimates may be completely unreliable. It may be desirable to have a relatively small, inexpensive, and portable ultrasound imaging system to aid in observing subcutaneous tissues.

Ultrasound may be used to search for internal defects in metallic or ceramic parts in a broad variety of industrial applications. Current systems may be cost effective, but may be unwieldy and acquire limited data, making it difficult to ensure that a thorough search has been performed. It may be desirable to have a relatively small, inexpensive, and portable ultrasound imaging system to aid in non-destructive evaluation.

Furthermore, new users may expect ultrasound images to produce representations parallel to the skin's surface, i. e. C-Scan images. It would be desirable for a low cost, system to be capable of producing C-Scan images. It may further be desirable to display data in the intuitive C-scan format to allow clinicians with little or no training in reviewing ultrasound images to make use of the device.

Ultrasound imaging devices may be too expensive for some applications. It may be desirable for a beamformer to be fabricated using large scale integration to enable the system to be produced at a lower cost.

Ultrasound imaging devices may be insufficiently portable for some applications. It may be desirable for an ultrasonic imaging device to be of a small size to make it easy to carry the device in a pocket or on a belt attachment. This may make the device as convenient as a stethoscope and will thus open new applications. It may be desirable for a beamformer to be fabricated using large scale integration to enable the system to be portable.

Figure 2:
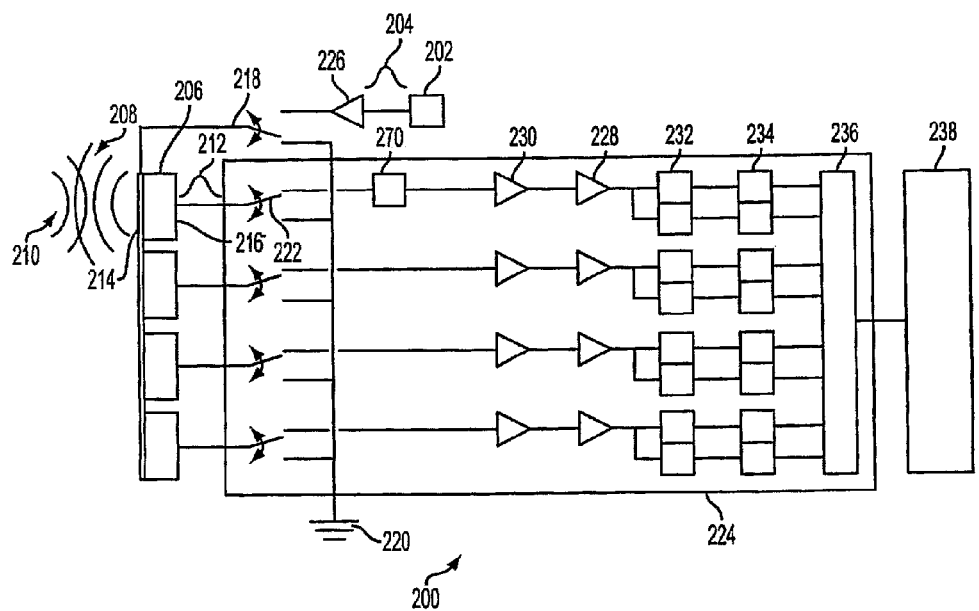
FIG. 2 is a schematic diagram of an ultrasonic transducer drive according to a first embodiment of the invention.
Figure 6:
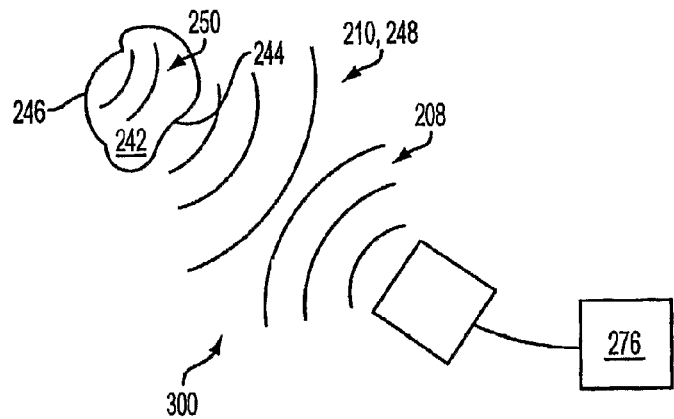
FIG. 6 is a schematic diagram of an ultrasonic imaging system for use with in an embodiment of the invention.

In FIG. 2 is shown an ultrasonic transducer drive 200 according to a first embodiment of the invention. Ultrasonic transducer drive 200 may be used in a relatively small, inexpensive, and portable ultrasound imaging system 300 such as that shown in FIG. 6. Ultrasonic transducer drive 200 may include a signal generator 202 for producing an outgoing signal 204. In several embodiments, outgoing signal 204 may be an electrical signal, an electro-magnetic signal, or an optical signal.

If outgoing signal 204 is an optical signal, cross-talk between the circuits of ultrasonic transducer drive 200 may be reduced or eliminated, since optical signals do not, in general, interfere with one another. This may allow ultrasonic transducer drive 200 to be made smaller than an equivalent electronic device by increasing the density of the circuits. in one case, outgoing signal 204 may be processed as an optical signal and converted to an electrical signal to drive a transducer. An integrated circuit comprising ultrasonic transducer drive 200 may be fabricated out of gallium-arsenide (GaAs) so that the both the optical circuits and the electrical circuits can be fabricated on the same device. In another case, a transducer utilizing sono-luminescence to convert light directly into sound may be used, dispensing entirely with any need for an electrical-optical interface.

In several embodiments, signal generator 202 may be a storage device, such as a read-only memory (ROM), an oscillator such as a crystal oscillator, a resonant circuit such as a resistor-inductor-capacitor (RLC) or tank circuit, a resonant cavity such as a ruby laser or a laser diode or a tapped delay line.

In the event that signal generator 202 is a storage device, outgoing signal 204 may have been stored previously, to be read out when needed. In this embodiment, several versions of outgoing signal 204 may be stored for use with various objects 242 to be imaged. Ultrasonic transducer drive 200 may thus be set to produce a signal appropriate for a particular object 242 to be imaged by choosing one of the stored versions of outgoing signal 204.

In the event that signal generator 202 is an oscillator, outgoing signal 204 may be a sinusoid of varying frequencies. In this case, outgoing signal 204 may be generated at an arbitrarily high clock speed and still be forced through filters of arbitrarily small bandwidth. This may be advantageous, for example, if a wide band signal is inconvenient. A resonant circuit or a resonant cavity may work in a similar manner. Furthermore, an oscillator may be used to produce a range of frequencies, from which a frequency that generates an optimum response may be selected.

In the event that signal generator 202 is tapped delay line, outgoing signal 204 could be generated in a manner similar to a spreading code in a code division multiple access (CDMA) format cell phone system. In this case outgoing signal 204 would not need to be a pure sinusoid, but may be a code with a fixed repetition length, such as a Walsh or a Gold code. This may, for example, allow an autocorrelation length of outgoing signal 204 to be adjusted to enhance or suppress coded excitation of an incoming signal.

If signal generator 202 is a tapped delay line it may be followed by an equalizer to bias or pre-emphasize a range of frequencies in outgoing signal 204. In one embodiment, the equalizer may be an adaptive equalizer that operates on an incoming signal analogous to the sound reflected by the imaged object 242. In this case, the incoming signal could be measured and the result applied to the adaptive equalizer to compensate for frequency attenuation of the sound by amplifying one or more frequencies of the incoming signal or outgoing signal 204 as necessary. This may be useful if, for example, object 242 attenuates or absorbs sound to the point that no return signal is available for imaging. In one embodiment, the adaptive equalizer could be placed in parallel with signal generator 202 and in series with the incoming signal.

In one embodiment, an equalizer could be placed in series with signal generator 202. In this case the equalizer could emphasize a particular frequency or frequencies in outgoing signal 204. The equalizer may, for example, place a bias or pre-emphasis toward lower frequencies on outgoing signal 204. This embodiment may be appropriate if, for example, object 242 to be imaged is expected to have features that attenuate lower frequencies significantly more than higher frequencies to the extent that imaging may be difficult. The converse may be true as well, in that the equalizer may have a bias or pre-emphasis toward higher frequencies.

In one embodiment, signal generator 202 may include a generator amplifier 226 for amplifying outgoing signal 204. Generator amplifier 226 may pre-emphasize certain frequencies of outgoing signal 204 to suit the attenuation characteristics of object 242 to be imaged as well. Signal generator 202 may also include an oscillator to produce an appropriate modulation frequency, such as a radio frequency (RF) signal, with which to modulate outgoing signal 204.

Ultrasonic transducer drive 200 may also include a transducer 206 for converting outgoing signal 204 to outgoing ultrasound 208 at a frequency of outgoing signal 204. In one embodiment, transducer 206 may have a transmit side 214 forming an interface with outgoing signal 204. In several embodiments, transducer 206 may be a piezoelectric element, a voice coil, a crystal oscillator, a sono-luminescent transducer, or a Hall effect transducer. In one embodiment, reversals of outgoing signal 204 produce vibration of a surface of transducer 206 at substantially the frequency of outgoing signal 204. In another embodiment, reversals of outgoing signal 204 produce vibrations of a surface of transducer 206 at frequencies that are significantly higher or lower than the frequency of outgoing signal 204, such as harmonics of outgoing signal 204. This vibration may, in turn, produce successive compressions and rarefactions of an atmosphere surrounding the surface of transducer 206, also at substantially the frequency of outgoing signal 204. If the frequency of outgoing signal 204 is substantially higher than a frequency at which sound may be heard, the successive compressions and rarefactions of the atmosphere may be termed ultrasound.

In one embodiment, transmit side 214 may be connected operably to a transmit switch 218. In several embodiments, transmit switch 218 may be an electronic switch, an optical switch, a micro-mechanical switch, a transistor, a field-effect transistor (FET), a bi-polar transistor, a metal-oxide-semiconductor (MOS) transistor, a complementary metal-oxide-semiconductor (CMOS) transistor, a metal-oxide-semiconductor field-effect transistor (MOSFET), or a clamp diode. Transmit switch 218 may be connected switchably to signal generator 202 and a reference potential 220.

If outgoing ultrasound 208 is reflected by object 242, some of outgoing ultrasound 208 may return to ultrasound imaging system 300 as reflected ultrasound 210. In one embodiment, outgoing ultrasound 208 may be delayed or attenuated partially by object 242. A first portion 248 of outgoing ultrasound 208, for example, may be reflected immediately upon encountering a nearer surface 244 of object 242 while a second portion 250 of outgoing ultrasound 208 is not reflected until it encounters a further surface 246 of object 242. A round trip of second portion 250 will thus be longer than a round trip of first portion 248, resulting in a delay of second portion 250 relative to first portion 248, as well as delays of both first and second portions 248,250 relative to outgoing ultrasound 208. Furthermore, second portion 250 may be damped or attenuated by a material of object 242. The delays may be measured for disparate points of object 242, producing an image 276 of object 242.

In one embodiment, transducer 206 may convert at least a portion of reflected ultrasound 210 to an incoming signal 212. In several embodiments, incoming signal 212 may be an electro-magnetic signal, an electrical signal, or an optical signal. In one embodiment, transducer 206 may have a receive side 216 forming an interface with incoming signal 212.

In one embodiment, receive side 216 may be connected operably to a receive switch 222. In several embodiments, receive switch 222 may be an electronic switch, an optical switch, a micro-mechanical switch, a transistor, a field-effect transistor, a bi-polar transistor, a MOS transistor, a CMOS transistor, a MOSFET, or a clamp diode. Receive switch 222 may be connected switchably to a signal receiver 224 and reference potential 220.

In one embodiment, signal receiver 224 may include a receiver amplifier 228 for amplifying incoming signal 212. In one embodiment, signal receiver 224 may further comprise a receiver pre-amplifier 230 for amplifying incoming signal 212. In one embodiment, signal receiver 224 may include a sample-and-hold 232 for discretizing an amplitude of incoming signal 212. In one embodiment, signal receiver 224 may include an analog-to-digital A/D converter 234 for converting incoming signal 212 to a digital signal.

In one embodiment, signal receiver 224 may further comprise a filter 270, such as an analog "brick wall" filter, for filtering out-of-band frequencies from incoming signal 212. Filter 270 may be placed ahead of pre-amplifier 230 or receiver amplifier 228, or both, to protect A/D converter 234 from large out-of-band dynamics. Filter 270 may be dispensed with if, on the other hand, A/D converter 234 is fast enough to tolerate large out-of-band frequencies. In this case, incoming signal 212 could be converted directly to the digital domain, and the number of off-chip components could be reduced.

In one embodiment, signal receiver 224 may include a register 236 for storing incoming signal 212. In one embodiment, signal receiver 224 may include a digital signal processor 238 for processing incoming signal 212. In one embodiment, signal receive switch 222 and signal receiver 224 may be implemented as an integrated circuit. In another embodiment, any or all of the components of signal receiver 224 beyond A/D converter 234 may be implemented in software on a microprocessor. Implementation of signal receiver 224 as an IC or in software may reduce system size and complexity, and may require only a single common connection on transmit side 214 of transducer 206. Thus transmit complexity may be reduced, but transmit focusing may also be rendered difficult or impractical. Simulations, however, have shown that reasonable spatial and contrast resolution may achieved through receive focusing alone while maintaining reasonable signal to noise ratios (SNR). One example of such a receive-side focusing scheme is described in the above-mentioned U.S. Provisional Application Ser. No. 60/439,990.

In one embodiment, transmit switch 218 may connect transmit side 214 to signal generator 202 for a first predetermined period of time while signal generator 202 generates outgoing signal 204. In this embodiment, receive switch 222 may connect receive side 216 to signal receiver 224 for a second predetermined period of time while signal receiver 224 receives incoming signal 212. Transmit switch 218 may connect transmit side 214 to reference potential 220 during substantially second predetermined period of time while signal receiver 224 receives incoming signal 212, and receive switch 222 may connect receive side 216 to reference potential 220 during substantially first predetermined period of time while signal generator 202 generates outgoing signal 204.

Figure 3:
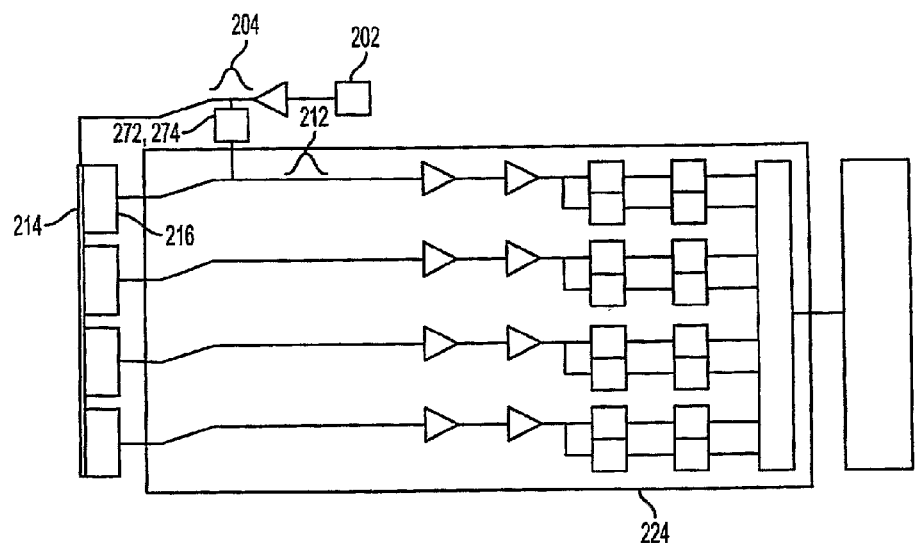
FIG. 3 is a schematic diagram of an ultrasonic transducer drive according to a second embodiment of the invention.

In a second embodiment, shown in FIG. 3, signal receiver 224 may receive incoming signal 212 while signal generator 202 is generating outgoing signal 204, in the manner of a full-duplex transceiver. In this embodiment, transmit switch 218 and receive switch 222 may be dispensed with, and outgoing signal 204 may be coupled to transmit side 214 while signal receiver 224 is coupled to receive side 216. In this embodiment, an echo canceller 272 may be inserted between outgoing signal 204 and incoming signal 212 to isolate incoming signal 212 from outgoing signal 204. Echo canceller 272 may be an equalizer, such as an adaptive equalizer. A voltage regulator 274, such as a diode running in reverse breakdown mode, may also isolate pre-amplifier 230 or receiver amplifier 228 from the high. voltage levels of outgoing signal 204.

Figure 4:
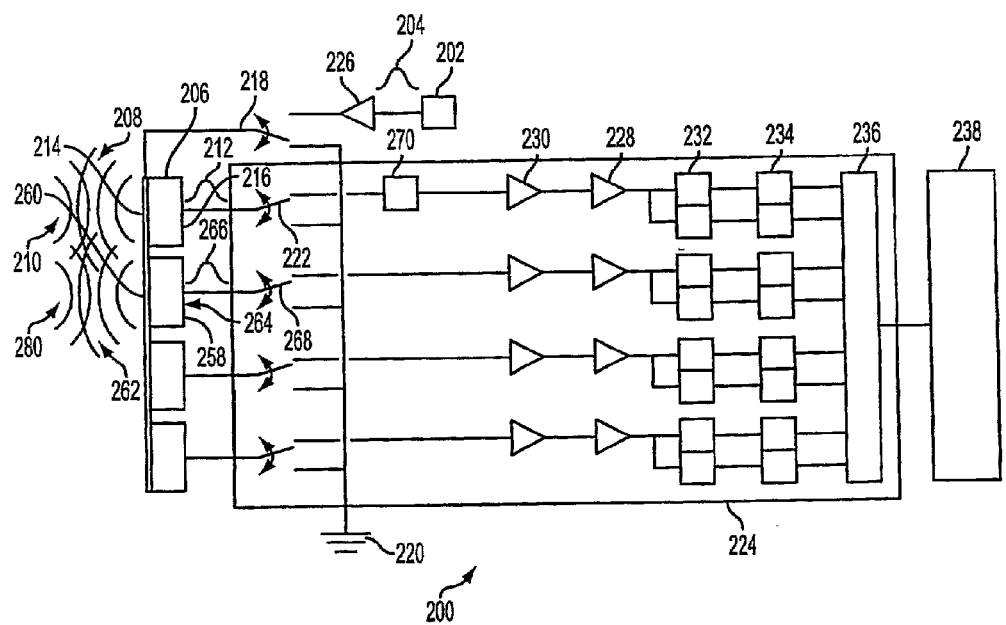
FIG. 4 is a schematic diagram of an ultrasonic transducer drive according to a third embodiment of the invention.

In a third embodiment, shown in FIG. 4, ultrasonic transducer drive 200 may also include a second transducer 258 having a second transmit side 260 for converting outgoing signal 204 to a second outgoing ultrasound 262 and a second receive side 264 for converting at least a portion of reflected ultrasound 210 and at least a portion of second reflected ultrasound 242 to a second incoming signal 266. In this embodiment, second transmit side 260 may be connected operably to transmit switch 218 so transmit switch 218 can connect second transmit side 260 switchably to signal generator 202 for substantially first predetermined period of time and connect second transmit side 260 to reference potential 220 for substantially second predetermined period of time. In this embodiment, second receive side 264 may be connected operably to a second receive switch 268 so second receive switch 268 can connect second receive side 264 switchably to signal receiver 224 for substantially second predetermined period of time and connect second receive side 264 to reference potential 220 for substantially first predetermined period of time. Incoming signal 212 and second incoming signal 266 are thus carried over separate channels to signal receiver 224. In one embodiment, signal receive switch 222, second receive switch 268, and signal receiver 224 may be implemented as an integrated circuit.

Figure 5:
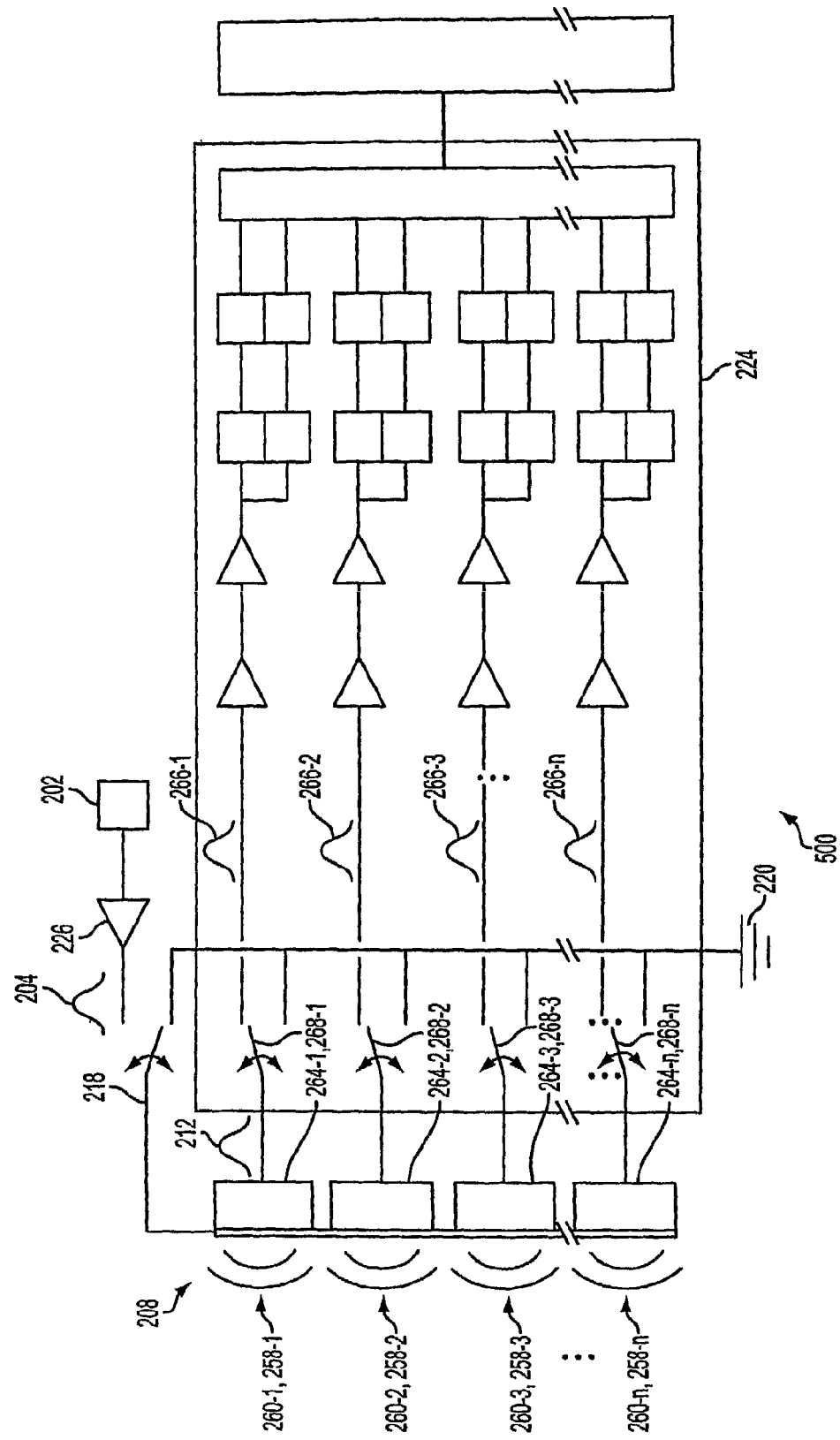
FIG. 5 is a schematic diagram of an ultrasonic transducer drive according to a fourth embodiment of the invention.

In a fourth embodiment, shown in FIG. 5, ultrasonic transducer drive 200 may include an array of transducers 258-1-258-$n$, each having a transmit side 260-1-260-$n$ for converting outgoing signal 204 to outgoing ultrasound 208 and a receive side 264-1-264-$n$ for converting at least a portion of reflected ultrasound 210 to incoming signals 266-1-266-$n$. In this embodiment, each transmit side 260-1-260-$n$ may be connected operably to transmit switch 218 so transmit switch 218 can connect all of transmit sides 260-1-260-$n$ switchably to signal generator 202 for substantially first predetermined period of time and connect all of transmit sides 260-1-260-$n$ to reference potential 220 for substantially second predetermined period of time. In this embodiment, each receive side 264-1-264-$n$ may be connected operably to a separate receive switch 268-1-268-$n$ so each receive switch 268-1-268-$n$ can connect each receive side 264-1-264-$n$ switchably to signal receiver 224 for substantially second predetermined period of time and connect each receive side 264-1-264-$n$ to reference potential 220 for substantially first predetermined period of time. Receive switches 268-1-268-$n$ thus form an array, and each incoming signal 266-1-266-$n$ may be carried over a separate channel to signal receiver 224.

In a fourth embodiment of invention, a method of driving an ultrasonic transducer 206 may include the steps of generating an outgoing signal 204, connecting a receive side 216 of transducer 206 to a reference potential 220, transducing outgoing signal 204 to outgoing ultrasound 208 with transducer 206, disconnecting receive side 216 of transducer 206 from reference potential 220, receiving at least a portion of reflected ultrasound 210 at transducer 206, transducing reflected ultrasound 210 to an incoming signal 212 with transducer 206, and converting incoming signal 212 to an image.

In a fifth embodiment of invention, the method of driving an ultrasonic transducer 206 may further include the steps of switching transmit side 214 of transducer 206 to receive outgoing signal 204 while outgoing signal 204 is being generated, switching transmit side 214 of transducer 206 to reference potential 220 while reflected ultrasound 210 is being received, or switching receive side 216 of transducer 206 to signal receiver 224 while reflected ultrasound 210 is being received.

Figure 7:
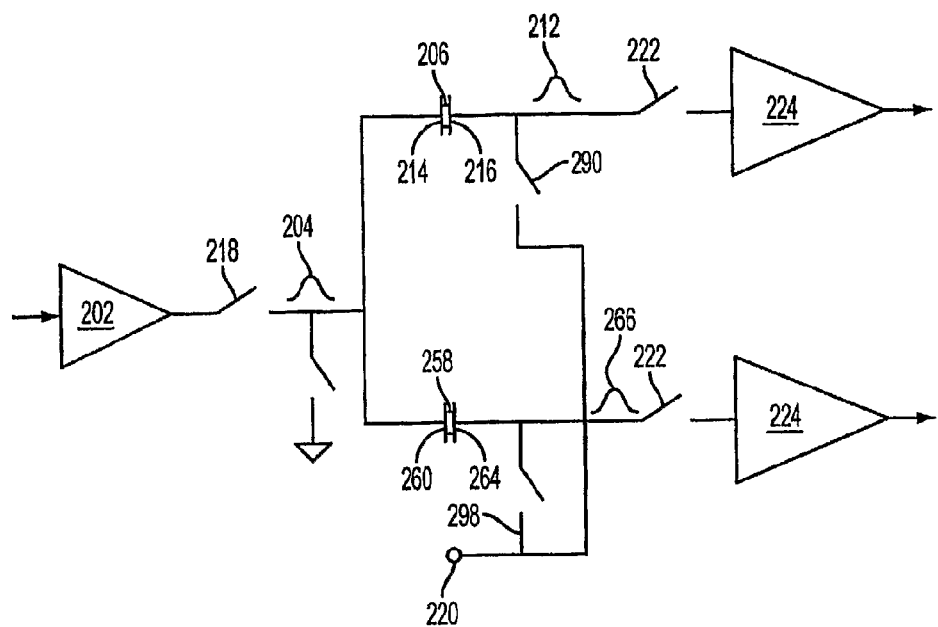
FIG. 7 is a schematic diagram of a possible transducer for use with in an embodiment of the invention.

In a sixth embodiment, shown in FIG. 7, ultrasonic transducer drive 700 may include transducer 206 for converting outgoing signal 204 to outgoing ultrasound 208 and for converting at least a portion of reflected ultrasound 210 to incoming signal 212. In one embodiment, transducer 206 may have transmit side 214 and receive side 216. In this embodiment, transmit side 214 may be connected conductably to signal generator 202 during at least first predetermined period of time, while receive side 216 may be connected conductably to signal receiver 224 during at least second predetermined period of time. In this embodiment, a shunt 290 may be connectable between receive side 216 and reference potential 220. In this embodiment, signal generator 202 may generate outgoing signal 204 during at least substantially first predetermined period of time while shunt 290 connects receive side 216 to reference potential 220. In this embodiment, signal receiver 224 may receive incoming signal 212 during substantially second predetermined period of time while shunt 290 may be substantially open. When the RX signal is asserted, the transducer common node is connected to ground and the receive signal is developed across the preamplifier input. When the TX signal is asserted, the off-chip transmit amplifier drives a large voltage pulse onto the common node of the array. During this transmit pulse, all of the transducer current is be shunted through the on-chip switching elements to the off chip voltage source reference potential 220.

In one embodiment, a second transducer 258 may have second transmit side 260 for converting outgoing signal 204 to second outgoing ultrasound 262 and second receive side 264 for converting at least a portion of reflected ultrasound 210 and at least a portion of second reflected ultrasound 242 to second incoming signal 266. In this embodiment, second transmit side 260 may be connected conductably to signal generator 202 during at least substantially first predetermined period of time. In this embodiment, second receive side 264 may be connected conductably to signal receiver 224 during at least substantially second predetermined period of time. In this embodiment, second shunt 290 may be connectable between second receive side 264 and reference potential 220. In this embodiment, second shunt 298 may connect second receive side 264 to reference potential 220 during at least substantially first predetermined period of time while signal generator 202 generates outgoing signal 204. In this embodiment, signal receiver 224 may receive second incoming signal 266 during substantially second predetermined period of time while second shunt 298 is substantially open.

In one embodiment, transmit side 214 may be connected operably to transmit switch 218, transmit switch 218 may be connectable switchably to signal generator 202 and to reference potential 220, and transmit switch 218 may connect transmit side 214 to signal generator 202 for substantially first predetermined period of time while signal generator 202 generates outgoing signal 204 and transmit switch 218 connects transmit side 214 to reference potential 220 for substantially second predetermined period of time.

In one embodiment, receive side 216 may be connected operably to receive switch 222, receive switch 222 may be connectable switchably to signal receiver 224, and receive switch 222 may connect receive side 216 to signal receiver 224 for substantially second predetermined period of time while signal receiver 224 receives incoming signal 212.

When incoming signal 212 is asserted, a common node of transducer 206 may be connected to reference potential 220 and incoming signal 212 may be developed across an input of pre-amplifier 230. When outgoing signal 204 is asserted, on the other hand, generator amplifier 226 may drive a large voltage pulse onto the common node of transducer 206.

In one embodiment, substantially all of outgoing signal 204 may be shunted through the on-chip switching elements to the off chip voltage source RecBias while outgoing signal 204 is being asserted. For a 100 V outgoing signal 204 with a 25 ns rise time and a transducer 206 capacitance of 4 pF, a peak current of 16 mA may have to be absorbed by each receive channel transmit switch 218. For a single channel this may be straightforward, but for a 1024 channel chip, over 16 Amperes of peak current may have to be shunted off chip! (Power dissipation may not be an issue since the duty cycle may be typically less than 0.1%.) An equivalent series resistance to RecBias may therefore be less than 0.2 ohms to keep on-chip voltage swings below 3V. The series inductance further exacerbates this problem. In one embodiment, the IC may be a dense ball-grid array package. In another embodiment, the IC may be a flip-chip solder bump arrangement. In this embodiment the IC may provide a large number of parallel shunting paths and minimize series inductance and resistance.

Simulations have shown that the on-chip switching elements made with standard CMOS transistors can be made compatible with the required peak shunting currents. Bipolar transistors are also capable of switching the required current levels. Transmit switch 218 and receive switch 222 can be made with commercially available high-voltage MOS or bipolar transistors.

It should also be clear that this may be compatible with multiple transmit signals. If the transducer fabrication is modified, one might create a transducer array with several transmit quadrants. This would allow some level of rudimentary transmit focusing while still reducing the number of high-voltage transmit circuits and simplify the protection of the receive circuits.

One skilled in the art would appreciate that a variety of tissue information may be obtained through judicious pulse transmission and signal processing of received echoes with the current invention. Such information could be displayed in conjunction with or instead of the aforementioned echo information.

One such type of information may be referred to as color flow Doppler as described in U.S. Pat. No. 4,573,477 to Namekawa et al., entitled "Ultrasonic Diagnostic Apparatus" hereby incorporated by reference herein in its entirety.

Another useful type of information may be harmonic image data as described in U.S. Pat. No. 6,251,074 to Averkiou et al., entitled "Ultrasonic Tissue Harmonic Imaging" and U.S. Pat. No. 5,632,277 to Chapman et al., entitled "Ultrasound Imaging System Employing Phase Inversion Subtraction to Enhance the Image," both of which are hereby incorporated by reference herein in their entirety. Yet another type of information that may be obtained and displayed may be known as Power Doppler as described in U.S. Pat. No. 5,471,990 to Thirsk, entitled "Ultrasonic Doppler Power Measurement and Display System" hereby incorporated by reference herein in its entirety.

Angular scatter information might also be acquired using a method described in a co-pending U.S. patent application Ser. No. 10/030,958, entitled "Angular Scatter Imaging System Using Translating Apertures Algorithm and Method Thereof" filed Jun. 3, 2002, of which is hereby incorporated by reference herein in its entirety. Speckle may be a common feature of ultrasound images. While it may be fundamental to the imaging process, many users find its appearance confusing and it has been shown to limit target detectability. A variety of so called compounding techniques have been described which could be valuable for reducing the appearance of speckle in ultrasound transducer drive images. These techniques include spatial compounding and frequency compounding, both of which are well described in the literature.

One skilled in the art would appreciate that the common practice of frequency compounding could be readily applied to the current invention. By transmitting a plurality of pulses at different frequencies and forming separate detected images using the pulses one may obtain multiple unique speckle patterns from the same target. These patterns may then be averaged to reduce the overall appearance of speckle.

The well known techniques of spatial compounding may also be applied to the current invention. The most conventional form of spatial compounding, which we call two-way or transmit-receive spatial compounding, entails the acquisition of multiple images with the active transmit and receive apertures shifted spatially between image acquisitions. This shifting operation causes the speckle patterns obtained to differ from one image to the next, enabling image averaging to reduce the speckle pattern.

In another technique, which we term one-way or receive-only spatial compounding, the transmit aperture may be held constant between image acquisitions while the receive aperture may be shifted between image acquisitions. As with two-way spatial compounding, this technique reduces the appearance of speckle in the final image.

In many ultrasound applications the received echoes from tissue have very small amplitude, resulting in an image with poor signal to noise ratio. This problem may be addressed through the use of a technique known as coded excitation. In this method the transmitted pulse is long in time and designed so that it has a very short autocorrelation length. In this manner the pulse is transmitted and received signals are correlated with the transmitted pulse to yield a resultant signal with good signal to noise ratio, but high axial resolution (short correlation length). This method could be readily applied in the present invention ultrasound transducer drive device and method to improve the effective signal to noise ratio. The coded excitation technique is described in U.S. Pat. No. 5,014,712 to O'Donnell, entitled "Coded Excitation for Transmission Dynamic Focusing of Vibratory Energy Beam" hereby incorporated by reference herein in its entirety.

An aspect in fabricating a system like the present invention ultrasound transducer drive is in construction of the transducer array. Both cost and complexity could be reduced by incorporating a transducer fabricated using photolithographic techniques, i. e. the transducer is formed using micro electro mechanical systems (MEMS). One particularly attractive approach has been described in U.S. Pat. No. 6,262,946 to Khuri-Yakub et al., entitled "Capacitive Micromachined Ultrasonic Transducer Arrays with Reduced Cross-Coupling" hereby incorporated by reference herein in its entirety.

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

Broad Scope of the Invention

While illustrative embodiments of the invention have been described herein, the present invention is not limited to the various preferred embodiments described herein, but includes any and all embodiments having equivalent elements, modifications, omissions, combinations (e. g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language present invention or invention should not be improperly interpreted as an identification of criticality, should not be improperly interpreted as applying across all aspects or embodiments (i. e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed, "e.g." which means "for example;" and "NB" which means "note well."

What is claimed is:

1. An ultrasonic transducer drive, comprising:
a signal generator for producing an outgoing signal;
a transducer for converting said outgoing signal to outgoing ultrasound and for converting at least a portion of reflected ultrasound to an incoming signal, said transducer having a transmit side and a receive side;
said transmit side connected conductably to said signal generator during a first predetermined period of time;
said receive side connected conductably to a signal receiver during a second predetermined period of time; and
a shunt connectable between said receive side and a first reference potential;
wherein said signal generator is configured to generate said outgoing signal during said first predetermined period of time while said shunt is configured to connect said receive side to said first reference potential during said first predetermined period of time;
wherein said signal receiver is configured to receive said incoming signal during said second predetermined period of time while said shunt is configured to be open during said second predetermined period of time and while said transmit side is configured to connect to a second reference potential during said second predetermined period of time;
wherein said receive side is connected operably to a receive switch;
wherein said receive switch is connectable switchably to said signal receiver; and
wherein said receive switch is configured to connect said receive side to said signal receiver for said second predetermined period of time;
wherein said transmit side is connected operably to a transmit switch;
wherein said transmit switch is connectable switchably to said signal generator and to said second reference potential;
wherein said transmit switch is configured to connect said transmit side to said signal generator for said first predetermined period of time and said transmit switch is configured to connect said transmit side to said second reference potential for said second predetermined period of time;

wherein said reflected ultrasound is elicited by said outgoing ultrasound; and wherein said receive side is conductively isolated from said transmit side.

2. The ultrasonic transducer drive of claim 1, comprising further:

a second transducer having a second transmit side configured to convert said outgoing signal to a second ultrasound and a second receive side configured to convert at least a portion of said reflected ultrasound and at least a portion of second reflected ultrasound to a second incoming signal;

said second transmit side configured to connect conductably to said signal generator during said first predetermined period of time;

said second receive side configured to connect conductably to said signal receiver during said second predetermined period of time; and a second shunt connectable between said second receive side and said first reference potential;

wherein said second shunt is configured to connect said receive side to said first reference potential during said first predetermined period of time; and wherein said signal receiver is configured to receive said second incoming signal during said second predetermined period of time.

3. The ultrasonic transducer drive of claim 1, wherein said signal generator comprises a generator amplifier for amplifying said outgoing signal.

4. The ultrasonic transducer drive of claim 1, wherein said transmit switch is selected from the group consisting of:
an electronic switch, a micro-mechanical switch, a transistor, a field-effect transistor, a bi-polar transistor, a MOS transistor, a CMOS transistor, and a MOS FET.

5. The ultrasonic transducer drive of claim 1, wherein said receive switch is selected from the group consisting of:
an electronic switch, a micro-mechanical switch, a transistor, a field-effect transistor, a bi-polar transistor, a MOS transistor, a CMOS transistor, and a MOS FET.

6. The ultrasonic transducer drive of claim 1, wherein said signal receiver comprises a receiver amplifier for amplifying said incoming signal.

7. The ultrasonic transducer drive of claim 1, wherein said signal receiver comprises a receiver pre-amplifier for amplifying said incoming signal.

8. The ultrasonic transducer drive of claim 1, wherein said signal receiver comprises a sample-and-hold for discretizing an amplitude of said incoming signal.

9. The ultrasonic transducer drive of claim 1, wherein said signal receiver comprises an A/D converter for converting said incoming signal to a digital signal.

10. The ultrasonic transducer drive of claim 1, wherein said signal receiver comprises a register for storing said incoming signal.

11. The ultrasonic transducer drive of claim 1, wherein said signal receiver comprises a digital signal processor for processing said incoming signal.

12. The ultrasonic transducer drive of claim 1, wherein said outgoing signal is selected from the group consisting of: an electro-magnetic signal and an electrical signal.

13. The ultrasonic transducer drive of claim 1, wherein said incoming signal is selected from the group consisting of:
an electro-magnetic signal and an electrical signal.

14. The ultrasonic transducer drive of claim 1, wherein said transducer is selected from the group consisting of: a piezoelectric element, a voice coil, a crystal oscillator, and a Hall effect transducer.

15. The ultrasonic transducer drive of claim 1, wherein said signal receive switch and said signal receiver are implemented as an integrated circuit.

16. The ultrasonic transducer drive of claim 1, wherein the first reference potential and the second reference potential are the same reference potential.

17. A method of driving an ultrasonic transducer, comprising:

generating an outgoing signal during a first predetermined period of time;

switching a transmit side of said transducer to transmit said outgoing signal while said outgoing signal is being generated;

switching a receive side of a transducer to a first reference potential during said predetermined first period of time;

transducing said outgoing signal to outgoing ultrasound with said transducer during said predetermined first period of time;

switching said receive side of said transducer from said first reference potential to signal receiver while said reflected ultrasound is being received during a predetermined second period of time;

receiving at least a portion of reflected ultrasound at said transducer during said predetermined second period of time using said signal receiver;

switching a transmit side of said transducer to a second reference potential during said predetermined second period of time;

transducing said reflected ultrasound to an incoming signal with said transducer during said predetermined second period of time; and converting said incoming signal to an image;

wherein said reflected ultrasound is elicited by said outgoing ultrasound; and wherein said receive side is conductively isolated from said transmit side.

18. The method of driving an ultrasonic transducer of claim 17, comprising further:

connecting a second receive side of a second transducer to said first reference potential;

transducing said outgoing signal to a second outgoing ultrasound with said second transducer;

disconnecting said second receive side of said second transducer from said first reference potential;

receiving at least a portion of said reflected ultrasound and a portion of said second reflected ultrasound at said second transducer;

transducing said reflected ultrasound and said second reflected ultrasound to a second incoming signal with said second transducer; and converting said second incoming signal to an image.

19. The method of driving an ultrasonic transducer of claim 18, comprising further:

switching a second transmit side of said second transducer to transmit said outgoing signal while said outgoing signal is being generated.

20. The method of driving an ultrasonic transducer of claim 18, comprising further:

switching said second transmit side of said second transducer to said second reference potential while said reflected ultrasound and said second reflected ultrasound is being received.

21. The method of driving an ultrasonic transducer of claim 18, comprising further:
   switching said second receive side of said second transducer to said second signal receiver while said reflected ultrasound and said second reflected ultrasound is being received.

22. The method of driving an ultrasonic transducer of claim 17, comprising further amplifying said outgoing signal.

23. The method of driving an ultrasonic transducer of claim 17, comprising further an operation selected from the group consisting of:
   amplifying said incoming signal, pre-amplifying said incoming signal, discretizing an amplitude of said incoming signal, converting said incoming signal to a digital signal, storing said incoming signal, and processing said incoming signal.

24. The method of driving an ultrasonic transducer of claim 17, comprising further an operation selected from the group consisting of:
   viewing said image, guiding insertion of a needle based on said image, guiding insertion of a catheter based on said image, and guiding insertion of an endoscope based on said image.

25. The method of driving an ultrasonic transducer of claim 17, wherein the first reference potential and the second reference potential are the same reference potential.

26. A system for driving an ultrasonic transducer, comprising:
   means for generating an outgoing signal during first predetermined period of time;
   means for transducing said outgoing signal to outgoing ultrasound during said first predetermined period of time and reflected ultrasound to an incoming signal during a second predetermined period of time;
   means for switching a receive side of said transducer means to a reference potential during said first predetermined period of time;
   means for switching said receive side of said transducer means from said reference potential to a signal receiver while said reflected ultrasound is being received during said second predetermined period of time;
   means for switching a transmit side of said means for transducing said outgoing signal to a reference potential during said second predetermined period of time;
   means for converting said incoming signal to an image;
   wherein said reflected ultrasound is elicited by said outgoing ultrasound; and
   wherein said receive side is conductively isolated from said transmit side.

27. The system for driving an ultrasonic transducer of claim 26, comprising further means for amplifying said outgoing signal.

28. The system for driving an ultrasonic transducer of claim 26, comprising further means for amplifying said incoming signal.

29. The system for driving an ultrasonic transducer of claim 26, comprising further means for pre-amplifying said incoming signal.

30. The system for driving an ultrasonic transducer of claim 26, comprising further means for discretizing an amplitude of said incoming signal.

31. The system for driving an ultrasonic transducer of claim 26, comprising further means for converting said incoming signal to a digital signal.

32. The system for driving an ultrasonic transducer of claim 26, comprising further means for storing said incoming signal.

33. The system for driving an ultrasonic transducer of claim 26, comprising further means for processing said incoming signal.

34. The system for driving an ultrasonic transducer of claim 26, comprising further means for viewing said image.

35. The system for driving an ultrasonic transducer of claim 26, comprising further means for guiding insertion of a needle, a catheter, or an endoscope based on said image.

\* \* \* \* \*